United States Patent [19]

Schussler et al.

[11] Patent Number: 4,814,528

[45] Date of Patent: Mar. 21, 1989

[54] REMOVING WATER FROM CRUDE 1,2-DICHLOROETHANE COMPOSITIONS CONTAINING CHLORAL HYDRATE

[75] Inventors: Henry W. Schussler, North Canton, Ohio; W. Eugene Wimer, McMurray, Pa.

[73] Assignee: PPG Industries, Inc., Pittsburgh, Pa.

[21] Appl. No.: 780,154

[22] Filed: Sep. 26, 1985

[51] Int. Cl.$^4$ .............................................. L07C 17/38
[52] U.S. Cl. .................................................. 570/262
[58] Field of Search ......................................... 570/262

[56] References Cited

U.S. PATENT DOCUMENTS

| | | | |
|---|---|---|---|
| 2,584,036 | 1/1952 | Mahoney et al. | 202/42 |
| 2,746,912 | 5/1956 | Park et al. | 202/42 |
| 3,055,955 | 9/1962 | Hodges | 260/656 |
| 3,378,597 | 4/1968 | Dehn et al. | 260/652 |
| 3,427,359 | 2/1969 | Rectenwald et al. | 260/659 |
| 3,488,398 | 1/1970 | Harpring et al. | 260/659 |
| 3,679,373 | 7/1972 | Vancamp et al. | 23/288 L |
| 3,996,300 | 12/1976 | Ahlstrom | 260/652 P |
| 4,151,212 | 4/1979 | Rideout | 570/262 |
| 4,263,269 | 4/1981 | Little et al. | 423/488 |
| 4,513,152 | 4/1985 | Schillawski | 568/492 |

FOREIGN PATENT DOCUMENTS 1129942 5/1962 Fed. Rep. of Germany .

OTHER PUBLICATIONS

L. F. Albright, "Manufacture of Vinyl Chloride", *Chemical Engineering*, Apr. 10, 1967, pp. 219-224 and 226.
R. W. McPherson, C. W. Starks, and G. J. Fryar, "Vinyl Chloride Monomer . . . What You Should Know," *Hydrocarbon Processing*, Mar. 1979, pp. 75-88.

*Primary Examiner*—Howard T. Mars
*Attorney, Agent, or Firm*—George D. Morris

[57] ABSTRACT

The water content of crude 1,2-dichloroethane compositions containing chloral hydrate is reduced by stripping under superatmospheric pressure.

10 Claims, 1 Drawing Sheet

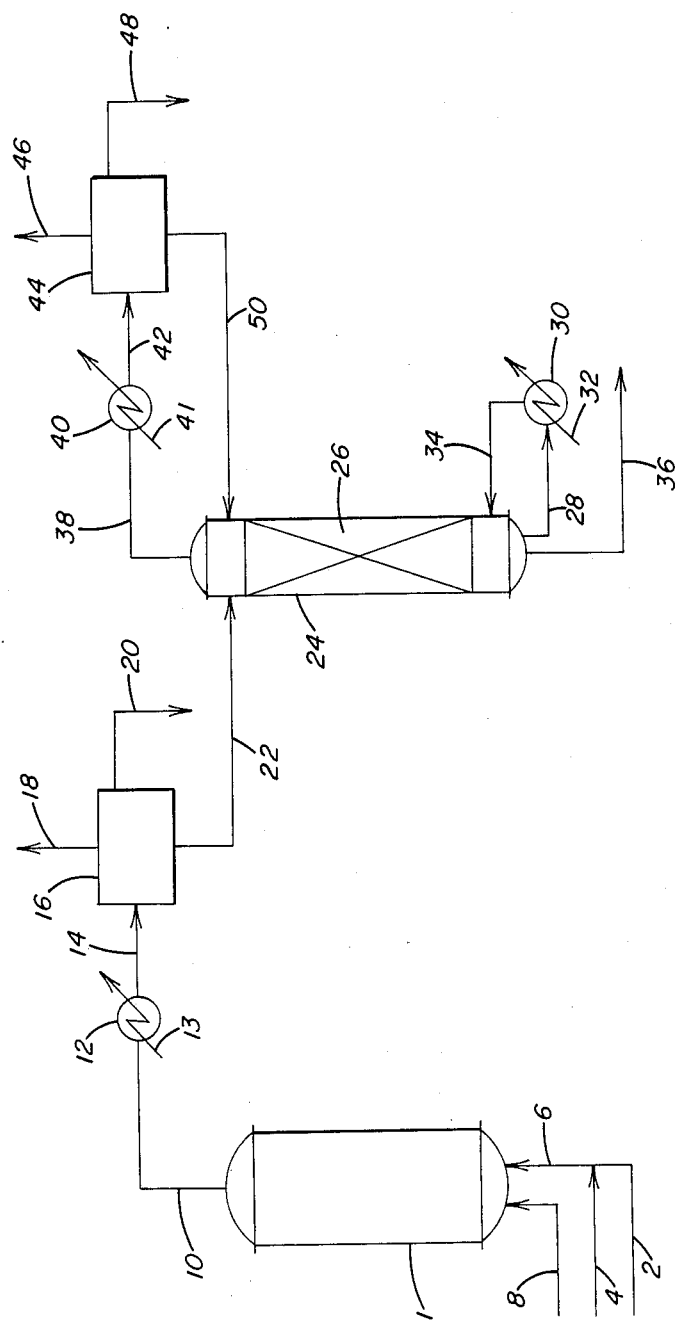

REMOVING WATER FROM CRUDE 1,2-DICHLOROETHANE COMPOSITIONS CONTAINING CHLORAL HYDRATE 1,2-Dichloroethane is frequently produced in a reactor system from which at least one stream of crude 1,2-dichloroethane comprising contaminating amounts of various impurities including chloral hydrate. Typical sources of such crude 1,2-dichloroethane include processes in which ethylene is oxychlorinated in packed bed, fluidized bed, or liquid phase reactors and processes in which ethane is oxychlorinated. See, for example, L. F. Albright, "Manufacture of Vinyl Chloride", *Chemical Engineering,* Apr. 10, 1967, pages 219–224 and 226, R. W. McPherson, C. M. Starks, and G. J. Fryar, "Vinyl Chloride Monomer . . . What You Should Know", *Hydrocarbon Processing,* March 1979, pages 75–88, and U.S. Pat. Nos. 3,055,955, 3,427,359; and 3,679,373, the entire disclosures of which are incorporated herein by reference, directed to oxychlorination.

Using the oxychlorination of ethylene as an example, ethylene, hydrogen chloride, and an oxygen containing gas (usually commercial oxygen, air, or oxygen-enriched air) are reacted to form a gas stream which is removed from the reactor and condensed to form two liquid phases, nne organic and the other aqueous. The liquid organic phase is substantially separated from the liquid aqueous phase and is forwarded as a crude 1,2-dichloroethane composition for further purification. The crude 1,2-dichloroethane composition comprises 1,2-dichloroethane as the principal constituent and contaminating amounts of impurities including chloral hydrate. In most cases the composition is saturated with water as it leaves the phase separator and also contains some hydrogen chloride. Inasmuch as chloral hydrate may be prepared by simply admixing anhydrous chloral and water, the chloral is principally present as chloral hydrate.

The crude 1,2-dichloroethane composition is typically forwarded to a purification system where the various components are separated using primarily several distillation operations. There are many systems that can be used, each differing from the others in the arrangement, numbers, identities, and functions of particular types of equipment. One factor common to all, however, is that 1,2-dichloroethane having a purity acceptable for the purposes of the manufacturer is produced. See, as examples, the article by McPherson, Starks, and Fryar and U.S. Pat. No. 3,055,955, both of which are referenced above. It has been found that if the chloral hydrate is allowed to remain in the crude 1,2-dichloroethane composition, its presence eventually gives rise to corrosive conditions that can damage equipment. Although it is not desired to be bound by any theory, it is believed that chloral hydrate decomposes to form anhydrous chloral and water and that the water then associates with small amounts of acidic materials such as the small amount of hydrogen chloride present, to form acid which is responsible for much of the corrosion. Corrosion can be reduced by constructing the equipment of corrosion resistant materials such as tantalum or glass, but the capital expenditures for such equipment are very high. In many cases the purification equipment is constructed of mild steel which is less expensive, and chloral hydrate is removed as an early step in the purification process. One such method of chloral hydrate removal is the treatment of the crude 1,2-dichloroethane composition with aqueous alkali metal hydroxide to produce alkali metal formate, chloroform and water, as shown in U.S. Pat. No. 3,378,597, the entire disclosure of which is incorporated herein by reference. In that method the effluent from the contacting tower is phase separated into organic and aqueous phases and the organic phase is forwarded to a distillation column where the crude 1,2-dichloroethane is essentially dehydrated. This procedure has been used successfully, but it is disadvantageous in that the alkali metal formate and chloroform by-products must eventually be disposed of or recovered.

Experience has shown that in the stripping of water from crude 1,2-dichloroethane compositions containing chloral hydrate by distillation conducted at or near ambient atmospheric pressure, (1) most of the chloral accompanies the 1,2-dichloroethane-containing bottoms product, and (2) the crude composition cannot ordinarily be dehydrated such that the 1,2-dichloroethane-containing bottoms product contains less than about 170 parts of water per million parts of the bottoms composition by weight. In this connection, the meanings of "chloral", "water", and their quantitative values should be clarified. The usual method for analyzing crude 1,2-dichloroethane compositions and other compositions which are predominately 1,2-dichloroethane, for water, is the Karl Fischer method. This method of analysis does not distinguish between free water and water combined with chloral as chloral hydrate. Therefore, the quantitative value of water given by this method includes both forms of water. Similarly, the usual method for analyzing crude 1,2-dichloroethane compositions and other compositions which are predominately 1,2-dichloroethane, for chloral is gas chromatography. This method does not distinguish between anhydrous chloral and chloral hydrate, and the quantitative value of chloral determined includes both the anhydrous chloral and the chloral of the chloral hydrate expressed on an anhydrous basis. As used throughout the present specification and claims, the terms "chloral" and "water" and their quantitative values will, when used in connection with the composition of crude 1,2-dichloroethane compositions and other compositions which are predominately 1,2-dichloroethane, be expressed on these bases, unless otherwise indicated or obvious from the context. It is believed that in the gas chromatographic method of analysis, the chloral hydrate is essentially decomposed into anhydrous chloral and water before the stream reaches the detector.

Although it is not desired to be bound by any theory, it is believed that the difficulty in dehydrating crude 1,2-dichloroethane compositions containing chloral hydrate by distillation at or near ambient pressure is because some of the chloral accompanying the 1,2-dichloroethane effluent is in the form of chloral hydrate.

Irrespective of theory, it has now been found that conducting the distillation of crude 1,2-dichloroethane compositions containing chloral hydrate under conditions of elevated pressure (and hence elevated temperature) can produce products having very low water contents. Accordingly, the invention is a method comprising (a) countercurrently contacting in a distillation apparatus a crude 1,2-dichloroethane composition which comprises 1,2-dichloroethane as the principal constituent and a contaminating amount of chloral hydrate, with reboiled vapors of 1,2-dichloroethane and chloral under superatmospheric pressure conditions of at least 55 kilopascals gauge, thereby substantially dehydrating the chloral hydrate, (b) removing from the apparatus at least one by-product composition which comprises water, and (c) removing from the apparatus at least one product composition which comprises 1,2-dichloroethane as the principal constituent and chloral, the product composition containing less than about 50 parts of water, whether free or combined with chloral as chloral hydrate, per million parts of the product composition by weight.

For a better understanding of the invention, reference may be made to the drawing which shows diagrammatically an embodiment of the invention.

The particular form of the distillation apparatus may vary widely. Examples of various distillation columns that may be used include bubble cap columns, sieve plate columns, packed columns, and similar devices.

In many cases the countercurrent contacting is conducted under superatmospheric pressure conditions of at least about 275 kilopascals gauge. Often the superatmospheric pressure is in the range of from about 55 to about 1725 kilopascals gauge. Preferably the superatmospheric pressure is in the range of from about 275 to about 560 kilopascals gauge.

In most cases the by-product composition also comprises 1,2-dichloroethane. Hence it is preferable to cool the by-product composition to produce a liquid organic phase and a liquid aqueous phase, to substantially separate the liquid organic phase from the liquid aqueous phase, and to introduce at least a portion of the separated liquid organic phase to the distillation apparatus as reflux. Preferably, substantially all of the separated liquid organic phase is introduced to the distillation apparatus as reflux.

The crude 1,2-dichloroethane composition which contains a contaminating amount of chloral hydrate and which is treated in accordance with the present invention ordinarily comprises at least about 90 percent by weight 1,2-dichloroethane. Often it comprises at least about 92 percent by weight 1,2-dichloroethane.

By a contaminating amount of chloral hydrate is meant more than a mere trace. The crude 1,2-dichloroethane composition usually comprises at least about 0.1 percent by weight chloral hydrate. Often the crude composition comprises at least about 0.2 percent by weight chloral hydrate. In many cases the chloral hydrate concentration is in the range of from about 0.1 to about 2 percent by weight. Frequently the chloral hydrate concentration is in the range of from about 0.2 to about 0.8 percent by weight. The crude composition may, and often does, include minor amounts of organic materials in addition to the chloral hydrate.

Frequently the crude 1,2-dichloroethane composition comprises water not combined with chloral as chloral hydrate (hereinafter "free water") as well as water combined with chloral as chloral hydrate. In such cases the crude 1,2-dichloroethane composition usually, but not necessarily, comprises at least about 0.01 percent by weight free water. Often the crude composition comprises from about 0.05 to about 0.3 percent by weight free water.

The crude 1,2-dichloroethane composition may originate from substantially any source which gives rise to chloral hydrate contamination, but in most cases it has originated at least in part from the oxychlorination of ethylene.

Preferably, the product composition contains less than about 35 parts of water, whether free or combined with chloral as chloral hydrate, per million parts of the product composition by weight.

After the product composition has been removed from the distillation apparatus, it may be introduced to one or more purification systems where the purity of the 1,2-dichloroethane is increased by removal of other materials. Usually at least a portion of the chloral is removed from the product composition. Distillation is most often used for this purpose.

Referring now in detail to the drawing, there is shown diagrammatically a reactor 1 in which ethylene is oxychlorinated to produce 1,2-dichloroethane. Ethylene from line 2 is admixed with hydrogen chloride from line 4 and the mixture passed through line 6 into reactor 1. Oxygen is passed through line 8 into reactor 1. The gaseous effluent from reactor 1 passes through line 10 to cooling system 12 where most of the effluent is condensed by coolant passing through line 13 to a liquid comprising an organic phase and an aqueous phase. The effluent is transferred through line 14 to phase separator 16 where the liquid phases are allowed to substantially separate into layers. Uncondensed gases may be removed through line 18. The upper liquid aqueous phase is removed through line 20 and may be dealt with as desired; for example, it may be processed to recover any of its components such as hydrogen chloride, and then discharged to an effluent treatment system. The lower liquid organic phase, which is a crude 1,2-dichloroethane composition comprising 1,2-dichloroethane as the principal constituent and a contaminating amount of chloral hydrate, is passed through line 22 to distillation column 24 containing packing material 26. In distillation column 24, and especially within the channels provided by packing material 26, 1,2-dichloroethane composition is countercurrently contacted with reboiled vapors of 1,2-dichloroethane and chloral under superatmospheric pressure conditions of at least 55 kilopascals gauge. Bottoms liquid is passed through line 28 to reboiler 30 heated by steam or other hot heat transfer fluid introduced to line 32. In reboiler 30 the bottoms liquid is boiled thereby producing the reboiled vapors which return to distillation column 24 through line 34. A portion of the bottoms liquid, which comprises 1,2-dichloroethane as the principal constituent and chloral, is removed through line 36 as a product composition. The product composition contains less than about 50 parts of water, whether free or combined with chloral as chloral hydrate, per million parts of the product composition by weight. A stream of gaseous by-product composition comprising water and 1,2-dichloroethane is removed from distillation column 24 through line 38 and introduced to condenser 40 cooled by coolant passing through line 41. In condenser 40 most of the by-product composition is condensed to a liquid comprising an organic phase and an aqueous phase. The material is transferred through line 42 to phase separator 44 where the liquid phases are allowed to substantially separate into layers. Uncondensed gases may be removed through line 46. The upper liquid aqueous phase is removed through line 48 and may be discarded or processed to recover any of its components. The lower liquid organic phase is passed through line 50 and introduced to distillation column 24 as reflux.

For the sake of clarity in setting forth the nature of the system, parts of the apparatus such as valves, pumps, flow indicators, pressure indicators, pressure reducers, temperature indicators, hold-up tanks, storage tanks, and the like, not essential to a complete understanding of the invention have been omitted from the drawing.

It will be appreciated that various modifications can be made to the system of the drawing without departing from the spirit of the invention. For example, the distillation column may be a bubble cap column, sieve plate column, or similar device. Sources of heat other than steam or hot heat transfer fluid may be used. Single condensers may be replaced with a plurality of condensers operating in series and/or parallel. Condensers may be vented to permit removal of uncondensed gases. Although distillation column 24 is shown operating as a stripping column, a rectifying section may be added above the feed point, if desired. Other modifications will be apparent to those skilled in the art.

The invention is further described in conjunction with the following example, which is to be considered illustrative rather than limiting.

EXAMPLE

Feed material was charged to a 4-liter holding vessel which was connected via polytetrafluoroethylene tubing to a variable flow feed pump. (Unless otherwise noted, all tubing used in the construction of the apparatus was 6.35 millimeter outside diameter polytetrafluoroethylene tubing having a wall thickness of 1.1938 millimeter.) The pump was equipped with a ceramic shaft and plastic head. A bypass was fitted to the pump discharge to provide added flow rate flexibility. The feed passed through a steam heated preheater consisting of 7.62 meters of tubing contained in a 0.61 meter section of 25.4 centimeter schedule 40 steel pipe. Steam was supplied to the preheater from a 965 kilopascal steam header and controlled with a needle valve. The heated feed material traveled from the preheater to one of the horizontal branches of a 2.54 centimeter borosilicate glass pipe cross attached to the top of the column. The column was constructed of 2.54 centimeter inside diameter borosilicate glass pipe, packed with 6.35 millimeter Berl Saddles. The packed height was 1.37 meters. The overhead material exited through the vertical branch of the cross into a tee to which nitrogen was added. The nitrogen, metered via a two stage regulator from cylinders through a needle valve, served to provide smooth pressure control and keep any organic material from the pressure transmitter. A rupture disk set at 690 kilopascals was attached to the nitrogen line to prevent overpressurization in case of a control valve failure. The combined overhead stream was introduced into a countercurrent double pipe condenser constructed of 61 centimeters of 12.7 millimeter outside diameter polytetrafluoroethylene tubing contained in 2.54 centimeter schedule 80 chlorinated poly(vinylchloride) pipe. Tap water circulating in the shell provided the cooling medium. The effluent from the condenser traveled to a phase separator mounted above the column. The phase separator was constructed from a 5.08 centimeter rotameter tube fitted with two steel-backed polytetrafluoroethylene flanges. Threaded rod fastened between the two flanges provided the means of sealing the rotameter tube to the polytetrafluoroethylene plates to hold system pressure. The top polytetrafluoroethylene plate was tapped through the side to provide an overflow for the aqueous phase. The condenser effluent was introduced into the phase separator through the top flange via tubing which terminated in the middle of the phase separator. The aqueous phase exited the phase separator into a small collector constructed of a 10.16 centimeter piece of 2.54 centimeter inside diameter borosilicate glass pipe. Polytetrafluoroethylene flanges were fitted to each end. A polytetrafluoroethylene valve was connected to the bottom flange to allow for aqueous material drainage at various intervals. In actual operation, this piece of equipment was unnecessary due to the small volume of aqueous material handled. The organic material from the phase separator was metered through a polytetrafluoroethylene needle valve and reintroduced into the second horizontal branch of the borosilicate glass cross. The reflux rate was adjusted to keep a constant organic level in the phase separator. A tee was inserted into the reflux line and connected to a polytetrafluoroethylene valve. This arrangement was used to measure the reflux rate at the end of each material balance run. In this instance, the reflux line valve was shut, and the purge line valve opened for a specified period of time such that the organic level in the phase separator remained constant. The collected material was weighed to determine the reflux rate.

A second borosilicate glass cross was attached to the bottom of the column. A polytetrafluoroethylene distributor plate drilled with 3.57 millimeter holes to provide a 75% open area was placed between the cross and the column. This served as a packing support and gas distributor. A 0.61 meter piece of flanged polytetrafluoroethylene lined stainless steel hose was fastened to the vertical branch of the cross via a polytetrafluoroethylene plate. This hose was bent in a U shape to provide the return loop for the thermosiphon reboiler. Heat input to the reboiler was provided by a 400 watt quartz electric heater. The polytetrafluoroethylene lined hose was traced with electrical heating tape to allow the desired boil-up to be attained with one heater. Each heat source was connected to a variable autotransformer to allow precise heat control. The quartz heater was inserted into the straight run of a borosilicate glass "Y" pipe and secured via a drilled out polytetrafluoroethylene fitting. The offset branch of the "Y" pipe was connected to the polytetrafluoroethylene lined stainless steel hose, and the other end of the straight run was connected to a 45° borosilicate glass elbow. This borosilicate glass elbow was connected to a horizontal branch of the bottom cross to complete the reboiler loop. The other horizontal branch of the cross provided the means for withdrawing the bottoms material. The bottoms material was cooled by passing through a length of tubing submerged in an ice water bath. The material flow rate was controlled by a level controller. When the liquid level in the column rose above the desired set point, the level controller tripped, opening a 6.35 millimeter polytetrafluoroethylene solenoid valve at the column bottom. The material was further cooled by passing through two water-cooled heat exchangers before being discharged into a collection vessel.

Crude 1,2-dichloroethane compositions fed to the column were produced by oxychlorinating ethylene using oxygen and hydrogen chloride to produce a reaction product, essentially condensing the reaction product, and phase separating the condensate to remove the aqueous phase. The feed materials therefore correspond to compositions flowing through line 22 of the drawing.

The distillation column was operated at both ambient atmospheric pressure and at a superatmospheric pressure of 414 kilopascals gauge, both being measured at the top of the column.

For each run, the crude 1,2-dichloroethane composition fed to the column was analyzed and the analytical results were summed. Each analytical result was then normalized by dividing the analytical result by the sum. Samples of the product composition were taken from time to time during each run. Each sample was analyzed and each analytical result was normalized as described in respect of the feed composition. The normalized analyses were then averaged.

The boil-up for each run was ascertained. The boil-up, expressed as percent, is one hundred times the mass flow rate of vapor passing from the top of the column to the condenser divided by the mass flow rate of the crude 1,2-dichloroethane composition fed to the column. Expressed in terms of the drawing, it is one hundred times the mass flow rate in line 38 divided by the mass flow rate in line 22.

The operating conditions and the results are shown in the Table. EDC is an abbreviation for 1,2-dichloroethane. A second set of samples was taken during Run 4 and these samples were analyzed at a different analytical laboratory; the results so obtained are shown in the second set of data for Run 4.

Although the present invention has been described with reference to specific details of certain embodiments thereof, it is not intended that such details should be regarded as limitations upon the scope of the invention except insofar as they are included in the accompanying claims.

TABLE

| Run | Operating Pressure, kPa Gauge | Boil-Up Percent | Normalized Feed Concentrations Weight Percent | | | | Average Normalized Product Concentration | | | | Mass Recovery Percent |
|---|---|---|---|---|---|---|---|---|---|---|---|
| | | | EDC | Chloral | Other Organics | Water | EDC, Wt. % | Chloral, Wt. % | Organics Wt. % | Water, PPM | |
| 1 | 414 | 19.7 | 93.52 | 0.890 | 5.333 | 0.254 | 95.86 | 0.862 | 3.279 | 34 | 97.68 |
| 2 | 0 | 8.2 | 94.47 | 1.005 | 4.264 | 0.261 | 94.95 | 1.10 | 3.933 | 174 | 96.4 |
| 3 | 0 | 41.4 | 95.13 | 0.847 | 3.779 | 0.242 | 95.71 | 0.926 | 3.342 | 236 | 101.50 |
| 4 | 414 | 51.5 | 98.01 | 0.739 | 1.047 | 0.200 | 98.31 | 0.735 | 0.955 | 32 | 97.27 |
| | 414 | 51.5 | 98.02 | 0.572 | 1.166 | 0.243 | 98.16 | 0.593 | 1.247 | 29 | 97.27 |

We claim:
1. A method comprising:
   (a) countercurrently contacting in a distillation apparatus a crude 1,2-dichloroethane composition which comprises 1,2-dichloroethane as the principal constituent and a contaminating amount of chloral hydrate, with reboiled vapors of 1,2-dichloroethane and chloral under superatmospheric pressure conditions of at least 55 kilopascals gauge, thereby substantially dehydrating said chloral hydrate,
   (b) removing from said apparatus at least one by-product composition which comprises water, and
   (c) removing from said apparatus at least one product composition which comprises 1,2-dichloroethane as the principal constituent and chloral, said product composition containing less than about 50 parts of water, whether free or combined with chloral as chloral hydrate, per million parts of said product composition by weight.

2. The method of claim 1 wherein
   (a) said by-product composition comprises 1,2-dichloroethane;
   (b) said by-product composition is cooled to produce a liquid organic phase and a liquid aqueous phase;
   (c) said liquid organic phase is substantially separated from said liquid aqueous phase;
   (d) at least a portion of said separated liquid organic phase is introduced to said distillation apparatus as reflux.

3. The method of claim 2 wherein substantially all of said separated liquid organic phase is introduced to said distillation apparatus as reflux.

4. The method of claim 1 wherein said crude 1,2-dichloroethane composition comprises a contaminating amount of free water.

5. The method of claim 1 wherein said crude 1,2-dichloroethane composition has originated at least in part from the oxychlorination of ethylene.

6. The method of claim 1 wherein said crude 1,2-dichloroethane composition comprises at least about 90 percent by weight 1,2-dichloroethane and at least about 0.1 percent by weight chloral hydrate.

7. The method of claim 6 wherein said crude 1,2-dichloroethane composition comprises at least about 0.01 percent by weight free water.

8. The method of claim 1 wherein said superatmospheric pressure conditions are of at least about 275 kilopascals, gauge.

9. The method of claim 1 wherein said product composition contains less thqn about 35 parts of water, whether free or combined with chloral as chloral hydrate, per million parts of said product composition by weight.

10. The method of claim 1 wherein at least a portion of said chloral is subsequently removed from said product composition.

* * * * *